United States Patent [19]

Latter et al.

[11] Patent Number: 4,981,874

[45] Date of Patent: Jan. 1, 1991

[54] MEDICAMENTS

[76] Inventors: Victoria S. Latter; Winston E. Gutteridge, both of Langley Court, Beckenham, Kent, England

[21] Appl. No.: 394,378

[22] Filed: Aug. 15, 1989

[30] Foreign Application Priority Data

Aug. 16, 1988 [GB] United Kingdom ................. 8819477

[51] Int. Cl.$^5$ ............................................. A61K 31/12
[52] U.S. Cl. .................................................... 514/682
[58] Field of Search ......................................... 514/682

[56] References Cited

U.S. PATENT DOCUMENTS

| 2,553,648 | 5/1951 | Fieser et al. | 514/682 |
| 3,347,742 | 10/1967 | Rogers | 514/682 |
| 3,367,830 | 2/1968 | Sarett | 514/682 |

FOREIGN PATENT DOCUMENTS

| 123238 | 9/1978 | European Pat. Off. | 514/681 |
| 0077551A2 | 4/1983 | European Pat. Off. | 514/682 |
| 0002228B1 | 2/1984 | European Pat. Off. | 514/682 |
| 0123239A2 | 11/1984 | European Pat. Off. | 514/682 |
| 0077550B1 | 7/1985 | European Pat. Off. | 514/682 |
| 1553424 | 9/1979 | United Kingdom | 514/682 |

OTHER PUBLICATIONS

Wofsy, Antimicrobial Therapy of Infections in Patients with Acquired Immunodeficiency Syndrome, pp. 377–401, Chapt. 36, 1986.

Fieser, et al., vol. 70, Oct. 1948, pp. 3156–3165, Naphthoquinone Antimalarials. II. Correlation of Structure and Activity Against *P. lophurae* in Ducks[1].

Hughes, Parasitology Today, vol. 3, No. 11, 1987, pp. 332–335, Treatment and Prophylaxis for *Pneumocystis carinii* Pneumonia.

Parsons, 7.8.89, Central RD & Misbeckenham Chemical Information Group Enquiry Report, Novelty Search for Naphthalenes and Naphthoquinones.

M. Pudney, et al., Hydroxynaphthoquinones As Antimalarials, 11 pages, Oct. 1987.

Victoria S. Latter, Discovery and Development of New Antimalarial Hydroxynaphthoquinones, 28 pages, Oct. 1987.

A. T. Hudson, Topics in Medicinal Chemistry, Antimalarial Hydroxynaphthoquinones, No. 65, pp. 266–283.

*Primary Examiner*—Jerome D. Goldberg
*Attorney, Agent, or Firm*—Donald Brown

[57] ABSTRACT

A method and certain compositions for treating *Pneumocystis carinii* infections in a mammal by administering a certain naphthoquinone compound or physiologically acceptable salts thereof.

20 Claims, No Drawings

MEDICAMENTS

The present invention relates to the treatment and prophylaxis of *Pneumocystis carinii* infections More particularly the invention is concerned with the use of 2-[4-(4-chlorophenyl)cyclohexyl-3-hydroxy-1,4-naphthoquinone in the treatment and prophylaxis of *Pneumocystis carinii* infections, the use of said compound for the manufacture of medicaments for the treatment and prophylaxis of *P.carinii* infections, and novel formulations containing said compound.

*Pneumocystis carinii* is a parasite which has a natural habitat in lung tissue. In a host with a normal immune system *P.carinii* is not considered to be pathogenic. However, when the immune system is defective *P.carinii* is liable to cause pneumonia. There is a variety of circumstances in which the immune system may be defective or deficient. Thus, for example immune system deficiency is common in immature or premature infants (neonates). It may also result from suppression by certain drugs, which may be deliberate e.g. in certain patients receiving organ transplants, or unavoidable e.g. as a side-effect of cancer chemotherapy. Disordered growth of one or more constituent parts of the immune system, e.g. as in certain forms of cancer, may also result in immunodeficiency.

Immune deficiency may furthermore be caused by viral infections, including human immunodeficiency virus (HIV). It has been reported (Hughes. W. T. (1987) Treatment and Prophylaxis of *Pneumocystis carinii* pneumonia, Parasitology Today 3(11) 332.335) that at least 60% of patients with acquired immunodeficiency syndrome (AIDS) suffer from *Pneumocystis carinii* pneumonia.

In this specification the term "immunocompromised host" will be used to describe hosts with a deficient or defective immune system.

Without treatment, *Pneumocystis carinii* pneumonia is almost always fatal in immunocompromised hosts The most widely used treatments for this condition are trimethoprim-sulphamethoxazole (cotrimoxaole) and pentamidine. However, both of these treatments have been reported to be only around 50-70% effective in AIDS patients and to produce a much higher than usual incidence of adverse reactions (about 50%) (Wofsy, C. B. Antimicrobial Agents Annual. 1986, Vol 1, p377-400). There is thus a need for new agents, especially for the prophylaxis of *P.carinii* pneumonia.

A wide range of naphthoquinones is known in the art. Such compounds have been variously described as having antimalarial, anticoccidial and antitheilerial activity. Some compounds have also been described as possessing activity against external parasites. Thus, Fieser et al. J. Amer. Chem. Soc. 1948, 70, 3156-3165 (and references cited therein) describes a large number of 2-substituted-3-hydroxy-1,4-naphthoquinones as having antimalarial activity. A number of these compounds have also been described in U.S. Pat. No. 2,553,648. Further classes of 2-substituted-3-hydroxy-1,4-naphthoquinones having activity as antimalarial, anticoccidial and/or antitheilerial agents are described in U.S. Pat. Nos. 3,367,830, and 3,347,742, U.K. Patent Specification No. 1553424, and European Patent Specifications Nos. 2 228, 77551 and 77550. European Patent Application No. 123239 discloses synergistic combinations of antiprotozoal naphthoquinones and 4-pyridinols or alkanoic esters thereof, which are said to be especially useful for the treatment or prophylaxis of malaria.

European Patent No. 123,238 discloses 2-substituted-3-hydroxy-1,4-naphthoquinones of formula (I)

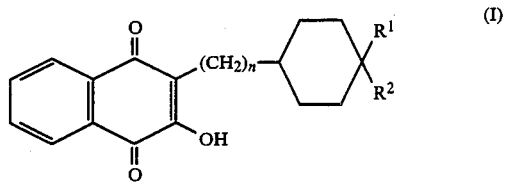

wherein either $R^1$ is hydrogen and $R^2$ is selected from $C^{1-6}$ alkoxy, aralkoxy, $C_{1-6}$ alkyl-$C^{1-6}$ alkoxy, phenyl substituted by one or two groups selected from halogen and $C_{1-6}$ alkyl, halogen and perhalo-$C^{1-6}$ alkyl or $R^1$ and $R^2$ are both $C^{1-6}$ alkyl or phenyl, and n is zero or 1, and physiologically acceptable salts thereof. Compounds of formula (I) wherein, n is zero are said to be active against the human malaria parasite *Plasmodium falciparum* and also against Eimeria species such as *E.tenella* and *E.acervulina*, which are causitive organisms of coccidiosis. Compounds of formula (I) where n is 1 are said to be active against protozoa of the genus Theileria, in particular *T.annulata* and *T.parva*. Amongst the compounds specifically named and exemplified is the compound of formula (I) wherein n is zero, $R^1$ is hydrogen and $R^2$ is 4-chlorophenyl, i.e. 2-[4-(4-chlorophenyl)cyclohexyl]-3-hydroxy-1,4-naphthoquinone.

We have now surprisingly found that 2-[4-(4-chlorophenyl)cyclohexyl]-3-hydroxy-1,4-naphthoquinone, represented in this specification by formula (II):

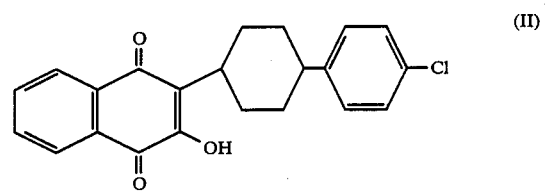

exhibits good activity in vivo against *Pneumocystis carinii* pneumonia infections in rats, and activity has also been demonstrated in an in vitro preparation of *P. carinii*.

Thus, in a first aspect the present invention provides the compound of formula (II) and physiologically acceptable salts thereof for uss in the treatment and/or prophylaxis of *Pneumocystis carinii* infections (e.g. *P.carinii* pneumonia) in mammals (including humans).

In another aspect the present invention provides the use of the compound of formula (II) and physiologically acceptable salts thereof for the manufacture of a medicament for the treatment and/or prophylaxis of *Pneumocystis carinii* infections in mammals (including humans).

According to a further aspect the present invention provides a method of treating and/or preventing *Pneumocystis carinii* infections which comprises administering to a mammal (including a human) suffering from or susceptible to infection with *P.carinii* an effective amount of the compound of formula (II), or a physiologically acceptable salt thereof.

Prevention of infections is particularly important in an immunocompromised host, as discussed hereinabove. In the case of immunosuppression resulting from HIV infection, prophylaxis may be required by those diagnosed as seropositive for HIV, and those with PGL (progressive generalised lymphadenopathy) or ARG (AIDS-related complex) as well as patients suffering from AIDS.

The hydroxyl group in the compound of formula (II) may form salts with appropriate bases, and physiologically acceptable salts of the compound (II) include inorganic base salts such as alkali metal (e.g. sodium and potassium) salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine.

It will be appreciated that the compound of formula (II) may exist as the cis or trans isomer, that is to say that the cyclohexyl ring may be cis or trans substituted by the naphthoquinone nucleus and the chlorophenyl group. Both cis and trans isomers and mixtures thereof in any ratio may be used in accordance with the present invention In general when the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required; typical mixtures include those in which the cis/trans isomer ratio is about 1:1,40:60 and 5:95. For use according to the present invention the trans isomer of the compound of formula (II) or a mixture of its cis and trans isomers containing at least 95% e.g. 99% of the trans isomer is preferred.

The compound of formula (II) may also exist in a tautomeric form in which the hydroxyl group donates its proton to one of the oxo groups and the use of such tautomeric forms is included within the scope of this invention. However, it is believed that the stable form is that shown in formula (II).

It will be appreciated that the amount of the compound of formula (II) or its salt required for use in the treatment or prophylaxis of *P.carinii* will depend inter alia on the route of administration, the age and weight of the mammal (e.g. human) to be treated and the severity of the condition being treated. In general, a suitable dose for administration to man for the treatment of *P.carinii* pneumonia is in the range of 0.1 mg to 200 mg per kilogram bodyweight per day, for example from 1 mg/kg to 100 mg/kg, particularly 10 to 50 mg/kg. For administration by inhalation the dose is conveniently in the range of 0.1 to 20 mg/kg/day, e.g. 0.5 to 10 mg/kg/day. It will be appreciated that for administration to neonates, lower doses may be required.

For prophylactic treatment the compound of formula (II) or its salt may also be given less frequently, e.g. as a single dose on alternate days, once or twice per week or once or twice per month. The dosage for prophylatic treatment will depend inter alia on the frequency of administration, and, where a depot preparation or controlled release formulation is used the rate of release of the active ingredient. Thus for once-weekly administration a suitable prophylactic dose is in the range 0.05 to 100 mg/kg, e.g. 0.05 to 50 mg/kg particularly 5 to 50 mg/kg.

For use according to the present invention the compound of formula (II) is preferably presented as a pharmaceutical formulation.

Pharmaceutical formulations comprise the active ingredient (that is, the compound of formula (II) or a physiologically acceptable salt thereof) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

The compound of formula (II) or its salt may conveniently be presented as a pharmaceutical formulation in unit dosage form. A convenient unit dose formulation contains the active ingredient in an amount of from 10 mg to 3g e.g. 10 mg to 1 g.

Pharmaceutical formulations include those suitable for oral, topical (including dermal, buccal and sublingual), rectal, parenteral (including subcutaneous, intradermal, intramuscular and intravenous), nasal and pulmonary administration e.g. by inhalation. The formulation may, where appropriate, be conveniently presented in discrete dosage units and may be prepared by any of the methods well known in the art of pharmacy. All methods include the step of bringing into association the compound of formula (II) or a physiologically acceptable salt thereof with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active ingredient in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredient, either alone or in admixture with one or more accessory ingredients, into the capsule shells and then sealing them in the usual manner. Cachets are analogous to capsules wherein the active ingredient together with any accessory ingredient(s) is sealed in a rice paper envelope. The compound of formula (II) or a physiologically acceptable salt thereof may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredient is formulated in an appropriate release—controlling matrix, or is coated with a suitable release—controlling film Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active ingredient with the softened or melted carrier(s) followed by chilling and shaping in moulds.

Pharmaceutical formulations suitable for parenteral administration include sterile solutions or suspensions of the active ingredient in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compound of formula (II) or a physiologically acceptable salt thereof may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing the active ingredient and desirably having a diameter in the range 0.5 to 7 microns are delivered into the bronchial tree of the recipient. Such formulations may be in the form of finely comminuted powders which may conveniently be presented in a pierceable capsule, suitably of, for example, gelatin, for use in an inhalation device, or as a self-propelling formulation comprising active ingredient, a suitable liquid or gaseous propellant and optionally other ingredients such as a surfactant and/or a solid diluent. Suitable liquid propellants include propane and the chlorofluorocarbons, and suitable gaseous propellants include carbon dioxide. Suitable surfactants include sorbitan trioleate (which is available for example under the trade name "Arlacel 85"). Polysorbate 20 and oleic acid. Self-propelling formulations may also be employed wherein the active ingredient is dispensed in the form of droplets of solution or supension. The self-propelling formulation typically contains from 0.05 to 20 mg/ml e.g. 0.1 to 5 mg/ml of the active ingredient.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility the active ingredient may be in the form of a solution or suspension for use in an atomiser or nebuliser whereby an accelerated airstream or ultrasonic agitation is employed to produce a fine droplet mist for inhalation. Such solutions or suspensions may comprise, in addition to the active ingredient and solvent(s), optional ingredients such as surfactants. Suitable surfactants include those described above for self-propelling formulations. The solution or suspension typically contains from 0.05 to 20 mg/ml e.g. 0.1 to 5 mg/ml of the active ingredient. When a suspension of the active ingredient is employed, the compound is preferably in finely divided form, e.g. in micronised form.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution or suspension.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

European Patent No. 123,238 contains no invitation to administer the compound of formula (II) by the nasal or pulmonary route nor any suggestion that the said compound, if administered in such a manner, would be effective in the treatment of the conditions therein taught; the said disclosure likewise contains no description of any formulation suitable for administration by the nasal or pulmonary route.

Pharmaceutical formulations of the compound of formula (II) adapted for administration by the nasal or pulmonary route thus represent novel formulations and form a further feature of the present invention.

The compound of formula (II) may also be used in accordance with the present invention in combination or concurrently with other therapeutic agents, for example agents used in the treatment of immunocompromised patients, including anticancer agents such as interferons e.g. alpha-interferon; antiviral agents such as azidothymidine (AZT,zidovudine), immunostimulants and immunodulators. The compound of formula (II) may also be administered in combination with a 4-pyridinol compound, as described in EPA No. 123,239 e.g. 3,5-dichloro-2,6-dimethylpyridinol (meticlorpindol). Methods for preparing the compound of formula (II) are described in EPNo. 123,238. The following example illustrates one such method, which, however, is not intended to limit the present invention in any way.

EXAMPLE 1

2-[b 4-(4-Chlorophenyl)cyclohexyl -3-hydroxy-1.4-naphthoquinone (a) 4-(4-Chlorophenyl)cyclohexane-1-carboxylic Acid Acetyl chloride (30 g) and finely powdered aluminium chloride (60 g) were stirred together in carbon disulphide (120 ml) and then cooled to $-50°$ C., in a $CO_2$/oxitol bath. Cyclohexene (30 g), previously cooled to $-50°$ C., was added dropwise during 10 minutes while maintaining the temperature of the reaction mixture at below $-20°$ C. The mixture was stirred at $-50°$ C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodimhydroxide and water, dried over anhydrous sodium sulphate and evaporated to dryness. The product was distilled in vacuo, the fraction boiling at 140–154° C. (0.1 mm Hg) collected, diluted with an equal volume of petroleum ether (40–60), cooled to −6° C. and a continuous stream of nitrogen gas bubbled through, and the separated colourless solid recovered.

Bromine (2.8ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl)cyclohexane-1-carboxylic acid, m.p. 254°–256° C.

(b) 2-[4-(4-chlorophenyl)cyclohexyl -3-chloro-1,4-naphthoquinone

A mixture of 2-chloro-1,4-naphthoquinone (3.95 g, 0.02 mol), 4-(4-chlorophenyl)cyclohexane-1-carboxylic acid (4.9 g, 0.02 mol) and powdered silver nitrate (1.05 g. 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours the cooled in ice for 30 mins, after which it was filtered, and the residual sticky solid extracted twice with boiling chloroform to remove inorganic material. The chloroform was removed by evaporation to leave a yellow-brown solid (ca 2.7 g). This was dissolved in 40 ml of boiling acetonitrile; a little insoluble material was removed by filtration.

On cooling, the title compound separated as yellow crystals, (550 mg) m.p. 172°–175° C.

(c) 2-[4-(4-chlorophenyl)cyclohexyl]-3-hydroxy-1,4-naphthoquinone

The product of stage (b) was suspended in 10 ml of boiling methanol and 0.55 g of potassium hydroxide in 5.5 ml of water was added dropwise over 15 mins. The mixture was refluxed until a dark red solution formed, (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200°–209°, were recrystallised from acetonitrile to give the title product as the trans-isomer (300 mg) m.p. 216°–219° C.

EXAMPLE 2

The following examples illustrate conventional pharmaceutical formulations which may be employed in accordance with the present invention:

A. Injectable Solution

A solution for intramuscular injection may be prepared by mixing:

| | |
|---|---|
| Compound of formula (II) | 9.5 parts by weight |
| Dimethyl sulphoxide | 19.0 parts by weight |
| Sorbitan monooleate | 4.5 parts by weight |

-continued

| | |
|---|---|
| Corn oil | 67.0 parts by weight |
| | 100.0 |

B. Injectable Solution

| | |
|---|---|
| Compound of formula (II) | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

C. Tablet

| | |
|---|---|
| Compound of formula (II) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

D. Oral Suspension

| | |
|---|---|
| Compound of formula (II) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

E. Injectable Suspension

| | |
|---|---|
| Compound of formula (II) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

F. Capsule

| | |
|---|---|
| Compound of formula (II) | 100 mg |
| Starch 1500 | 150 mg |
| Magnesium stearate | 2.5 mg |
| filled into a hard gelatin capsule | |

EXAMPLE 3

The following examples illustrate novel pharmaceutical formulations according to the present invention.

A. Suspension for Nebulisation

| | | |
|---|---|---|
| (a) Compound of formula (II), sterile | | 1.0 mg |
| Water for Injections | to | 10.0 ml |

Disperse the compound of formula (II) in the Water for Injections previously sterilised in a sterile container. Fill into sterile glass ampoules. 10 ml/ampoule under aseptic conditions, and seal each ampoule by fusion of the glass.

(b) The following suspension was prepared;

| Compound of formula (II), micronised | 1.0 g |
|---|---|
| Polysorbate 20 | 0.1% w/v |
| Water for Injections | to 10 ml |

The Polysorbate 20 was dispersed in the Water for Injections, followed by the compound of formula (II). This supension was filled into sterile glass ampoules, 10 ml/ampoule under aseptic conditions, and the ampoules sealed by fusion of the glass.

B. Aerosol Formulation

| (a) Compound of formula (II), micronised | 1.0 mg |
|---|---|
| Aerosol propellant | to 5.0 ml |

Suspend the micronised compound of formula (II) in the aerosol propellant. Fill this suspension into preformed aerosol cannisters, 5 ml/cannister under pressure, through the valve orifice.

| (b) Compound of formula (II), micronised | 1.0 mg |
|---|---|
| Arlacel 85 | 0.1% w/v |
| Aerosol propellant | to 5 ml. |

Disperse the Arlacel 85 in the aerosol propellant and then add compound of formula (II). Fill the suspension into preformed aerosol cannisters, 5 ml/cannister under pressure, through the valve orifice.

C. Powder Inhalation

| Compound of formula (II), micronised | 1.0 mg |
|---|---|
| Lactose | 29.0 mg |

Triturate and blend the micronised compound of formula (I) with the lactose. Fill the resulting powder blend into hard gelatin capsule shells, 30 mg per capsule.

D. Nasal Drops

| Compound of formula (II) | 100.0 mg |
|---|---|
| Methylhydroxybenzoate | 10.0 mg |
| Water for Injections | to 10.0 ml |

Disperse the compound of formula (II) and the methylhydroxybenzoate in the Water for Injections. Fill this suspension into suitable dropper bottles, 10 ml/bottle, and close by securing the dropper nozzle and bottle cap.

The use of the compound of formula (II) according to the present invention is illustrated by the following example:

BIOLOGICAL TEST RESULTS

Example 4

Activity Against *Pneumocystis carinii*

Test Compounds

A: 2-[trans-4-(4-chlorophenyl)cyclohexyl]-3-hydroxy-1,4-naphthoquinone

B: 2-[cis-4-(4-chlorophenyl)cyclohexyl]-3-hydroxy-1,4-naphthoquinone (a) Prophylaxis Groups of 10 rats were treated with dexamethasone to allow latent *Pneumocystis carinii* infection to develop. Tetracycline was also administered to protect against bacterial infections. Test compound A was administered, by gavage, from day 4 of the dexamethasone treatment, at a dose of 100 mg/kg/day. Two control groups of rats were treated with dexamethasone and tetracycline only. A further group of rats was given cotrimoxazole (trimethoprim+sulphamethoxazole, 50+250 mg/kg/day, orally) in place of the test compound.

At the end of the test period the animals were sacrificed and autopsies carried out The lungs were removed and the right lung bisected. An imprint was made onto microscope slides and stained with toluidine blue. One half of the lung was placed in formalin, processed in paraffin blocks, sectioned and stained by the Gomori methanamine silver nitrate method.

After autopsy the extent of *P.carinii* pneumonitis was scored under coded study as none if no organism seen; 1+ if *P.carinii* cysts seen sparsely distributed with less than one per 25 high power field (h.p.f.); 2+ if focal areas of *P.carinii* pneumonitis surrounded by 10 to 25 h.p.f. of normal lung and 3+if lung diffusely and extensively involved with organisms in almost all h.p.f.s.

RESULTS

| | No of Rats | Early deaths or cannibalisation | No of with P. carinii Pneumonitis | | | | No of rats with PCP/ No of rats tested |
|---|---|---|---|---|---|---|---|
| | | | None | 1+ | 2+ | 3+ | |
| Test Compound A | 10 | 2* | 8 | 0 | 2 | 0 | 0/8 |
| Control (1) | 10 | 2 | 0 | 1 | 2 | 5 | 8/8 |
| Control (2) | 10 | 0 | 0 | 0 | 2 | 8 | 10/10 |
| TMP/ SMZ | 10 | 0 | | | | | 0/10 |

*one early death, believed due to gavage, one cannibalisation.

(b) Prophylaxis

A further series of tests was carried out using the same general method as described above. Test compound A was administered at various dose levels, by gavage and in the diet.

The results are shown in Table 2.

TABLE 2

Extent of *P. carinii* after prophylaxis:
histopathology of lung sections (Gomori-Grocott stain)

| Group (Dose per kg/day) g = gavage, r = rations | No. of Rats Tested per Group | No. of Rats* Evaluated | No. with *P. carinii* Pneumonitis | | | | |
|---|---|---|---|---|---|---|---|
| | | | None | 1+ | 2+ | 3+ | Total No. |
| CONTROL: no drug | 10 | 9 | 0 | 1 | 0 | 8 | 9/9 |
| A: 200 mg (r) | 10 | 9 | 9 | 0 | 0 | 0 | 0/9 |
| A: 100 mg (r) | 10 | 10 | 10 | 0 | 0 | 0 | 0/10 |
| A: 100 mg (g) | 10 | 9 | 8 | 1 | 0 | 0 | 1/9 |
| A: 100 mg (g) | 15 | 9 | 9 | 0 | 0 | 0 | 0/9 |
| A: 50 mg (g) | 10 | 9 | 7 | 0 | 1 | 1 | 2/9 |
| A: 25 mg (g) | 10 | 8 | 1 | 2 | 1 | 4 | 7/8 |
| A: 10 mg (g) | 10 | 10 | 1 | 1 | 0 | 8 | 9/10 |
| TMP/SMZ: 50/250 mg (r) | 10 | 10 | 10 | 0 | 0 | 0 | 0/10 |

*Excludes accidental deaths (gavage) and cannibalised rats.

(c) Treatment

Groups of 10 rats were treated with dexamethasone and tetracycline for 4–6 weeks, as described in experiment (a) above. Three groups of rats were treated with Test compound A beginning after 4 weeks of immunosuppression, when *Pneumocystis carinii* pneumonia (PCP) had developed. Another group of rats in a parallel study was treated with Test compound A after 6 weeks of immunosuppression, when PCP infection was at an advanced stage. The results are shown in Table 3.

TABLE 3

Extent of *P. carinii* after prophylaxis:
histopathology of lung sections (Gomori-Grocott stain)

| Group (Dose per kg/day) g = gavage, r = rations | No. of Rats Tested per Group | No. of Rats* Evaluated | No. with *P. carinii* Pneumonitis | | | | |
|---|---|---|---|---|---|---|---|
| | | | None | 1+ | 2+ | 3+ | Total No. |
| <sup>a</sup>A: 100 mg (g) × 3 wk | 10 | 8 | 8 | 0 | 0 | 0 | 0/8 |
| <sup>a</sup>A: 50 mg (g) × 3 wk | 10 | 9 | 2 | 0 | 3 | 4 | 7/9 |
| <sup>a</sup>A: 25 mg (g) × 3 wk | 10 | 8 | 1 | 0 | 1 | 6 | 7/8 |
| CONTROL: no drug* | 10 | 10 | 0 | 1 | 3 | 6 | 10/10 |
| CONTROL: no drug | 10 | 9 | 0 | 1 | 0 | 8 | 9/9 |
| TMP/SMZ: 50/250 mg (r) × 3 wk | 10 | 10 | 8 | 1 | 1 | 0 | 2/10 |
| <sup>b</sup>A: 100 mg × 2 wk | 5 | 5 | 4 | 1 | 0 | 0 | 1/5 |
| CONTROL: no drug | 5 | 5 | 0 | 1 | 3 | 1 | 5/5 |

*5/10 rats sacrificed at 4 weeks of immunosuppression the time when therapeutic drugs were started.
Dexamethasone and tetracycline continued throughout experiment in all animals.
<sup>a</sup>Treatment with test compound started after 4 weeks of dexamethasone.
<sup>b</sup>Treatment with test compound started after 6 weeks of dexamethasone.

(d) Treatment

Groups of 15 rats were treated with dexamethasone and tetracycline for 4 weeks, as described in experiment (a) above. Test compounds (A) and (B) were administered orally by stomach tube from the beginning of week 5 to the end of week 7.

In parallel with each test compound, Celacol was administered to one group of rats as a control. The results are given in Table 4.

TABLE 4

| Test Compound | GROUP (Dose/kg/day) | SCORE 0 1 2 3 4 | NO. INFECTED/ NO. EXAMINED | % INFECTED |
|---|---|---|---|---|
| A | Celacol | 1 0 1 2 6 | 9/10 | 90 |
| | 50 mg/kg | 1 3 3 5 0 | 11/12 | 92 |
| | 75 mg/kg | 2 5 2 1 2 | 10/12 | 83 |
| | 100 mg/kg | 4 7 1 1 0 | 9/13 | 69 |
| A | Celacol | 0 8 7 0 0 | 12/15 | 100 |
| | 25 mg/kg | 3 7 4 1 0 | 12/15 | 80 |
| | 50 mg/kg | 1 6 4 2 0 | 12/13 | 92 |
| | 100 mg/kg | 4 6 2 0 0 | 8/12 | 67 |
| B | Celacol | 0 8 7 0 0 | 15/15 | 100 |
| | 25 mg/kg | 1 8 5 1 0 | 14/15 | 93 |
| | 50 mg/kg | 3 6 4 0 2 | 12/15 | 80 |
| | 100 mg/kg | 2 6 2 4 0 | 12/14 | 86 |

We claim:

1. A method of treating a *Pneumocystis carinii* infection in a mammal which comprises administering to said mammal having said infection an effective *Pneumocystis carinii* treatment amount of a naphthoquinone of the general formula (II):

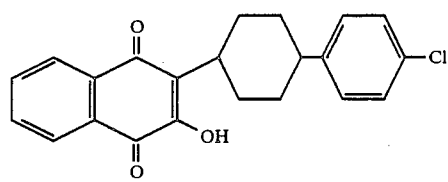

(II)

or a physiologically acceptable salt thereof.

2. A method according to claim 1 wherein in the compound 2-[trans-4-(4-chlorophenyl)cyclohexyl]-3-hydroxy-1,4-naphthoquinone or a physiologically acceptable salt thereof is administered.

3. A method according to claim 1 or claim 2 wherein the compound or salt of formula (II) is administered in an amount of from 10 to 50 mg per kilogram of mammal body weight per day.

4. A method according to claim 1 wherein the mammal is a human.

5. A method according to claim 2 wherein the mammal is a human.

6. A method according to claim 3 in which the mammal is a human.

7. A method of claims 1, 2, 3, 4, 5 or 6 in which the mammal has an HIV infection.

8. A method of treating *Pneumocystis carinii* infection in a mammal, which comprises administering to a mammal having said infection an effective *Pneumocystis carinii* treatment amount of 2-[trans-4-(4-chlorophenyl)cyclohexyl]-3-hydroxy-1,4-naphthoquinone.

9. A method according to claim 8, in which the mammal is a human.

10. A method according to claim 1, 2 or 8, wherein the compound of formula (II) or a physiologically acceptable salt thereof is administered nasally.

11. A method according to claim 1, 2 or 8, wherein the compound of formula (II) or a physiologically acceptable salt thereof is administered parenterally.

12. A method according to claim 1, 2 or 8, wherein the compound of formula (II) or a physiologically acceptable salt thereof is administered orally.

13. A method according to claim 1, 2 or 8, wherein the compound of formula (II) or a physiologically acceptable salt thereof is given by pulmonary administration.

14. A method according to claim 1, 2 or 8, wherein the infection is *Pneumocystis carinii* pneumonia.

15. A method of preventing *Pneumocystis carinii* infections in an immunocompromised mammal which comprises administering to said mammal an effective *P.carinii* prevention amount of a naphthoquinone of the general formula (II):

(II)

or a physiologically acceptable salt thereof.

16. A method according to claim 15 wherein the compound of formula (II) is 2-[trans-4-(4-chlorophenyl)cyclohexyl]-3-hydroxy-1,4-naphthoquinone or a physiologically acceptable salt thereof is administered.

17. A method according to claim 15 or claim 16 wherein the compound of formula (II) is administered in an amount of from 10 to 50 mg per kilogram of mammal body weight per day.

18. The method of claims 15, 16 or 17 in which the mammal has an HIV infection and is a human.

19. The method of claims 15, 16 or 17 in which the mammal is a human.

20. A method of preventing *Pneumocystis carinii* infections in an immunocompromised mammal, which comprises administering to said mammal an effective *Pneumocystis carinii* prevention amount of 2-[trans-4-(4-chlorophenyl)cyclohexyl]-3-hydroxy-1,4-naphthoquinone.

* * * * *